Sept. 19, 1967 P. ECKE Plant Pat. 2,768
POINSETTIA PLANT
Filed Aug. 8, 1966
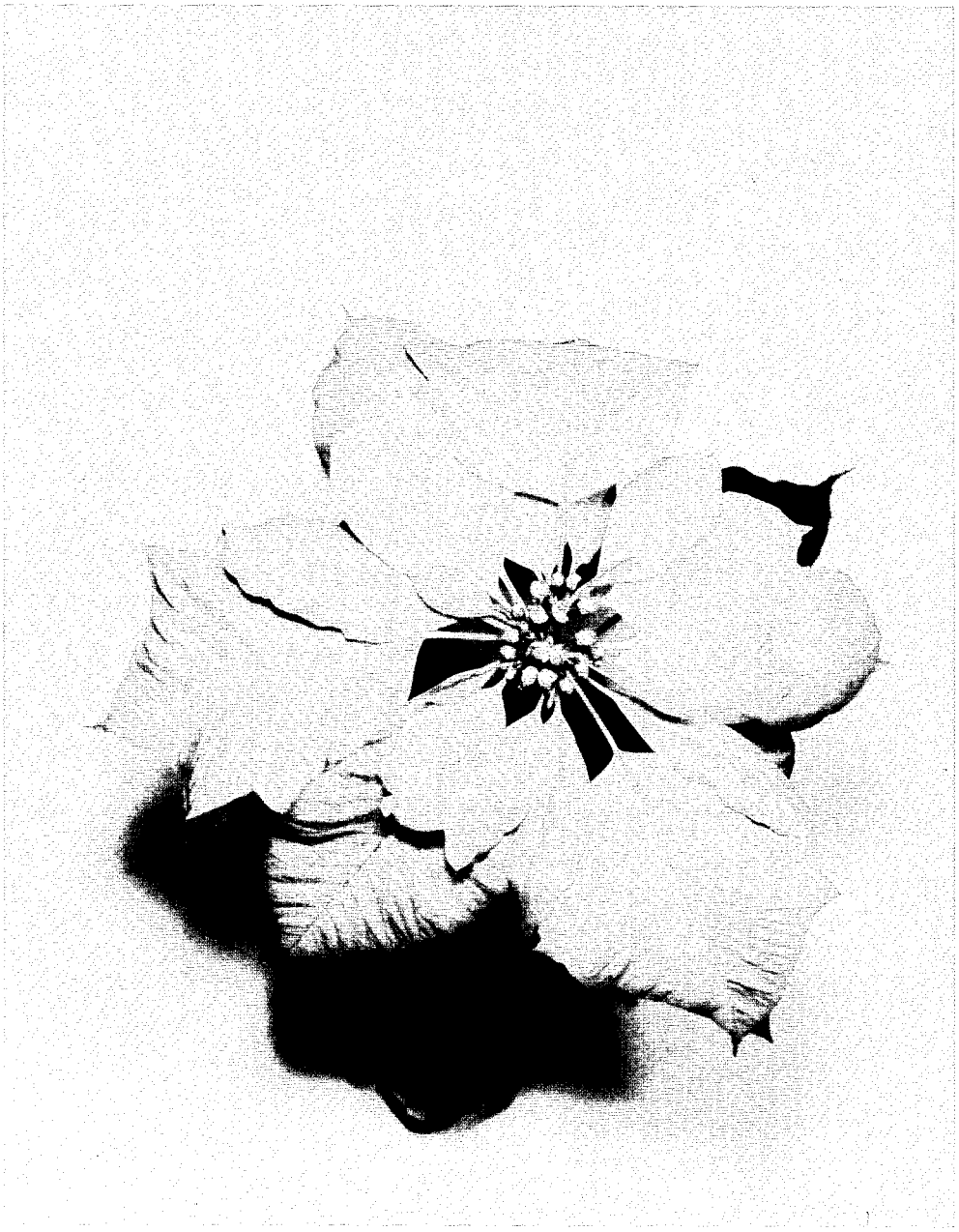
INVENTOR
PAUL ECKE
BY
ATTORNEY United States Patent Office Plant Pat. 2,768
Patented Sept. 19, 1967

2,768
POINSETTIA PLANT

Paul Ecke, P.O. Box 488, Encinitas, Calif. 92024

Filed Aug. 8, 1966, Ser. No. 571,373
1 Claim. (Cl. Plt.—86)

This invention relates to a new and distinctive variety of poinsettia plant (more specifically known botanically as *Euphorbia pulcherrima*). This new variety was originated by me as a hybrid seedling from selective cross-fertilization to combine, control and reproduce the advantages of two selected poinsettia plants.

Broadly, this new variety of poinsettia plant is distinguishable from its parent plants as well as from other known varieties of poinsettia plants, mainly in the outstanding desirable features which may be briefly stated as follows:

(1) The color of the bracts, which are subdued reddish-pink, rose tinted with mauve.

(2) The abundant proliferation of bracts and the variance in size and shape of the bracts in the involucre.

(3) The unusually long life of the bracts, inflorescence, and foliage leaves and the tenacity thereof to adhere to the peduncle.

(4) The variation in length of petioles of the several sizes and types of bracts.

(5) The relatively early natural blooming season, coupled with the long keeping qualities of bracts, inflorescence and foliage leaves, eliminating necessity for light treatment to delay development of bracts and inflorescence.

(6) An exceptionally vigorous and extensive root structure.

(7) A relatively long, stiff peduncle which requires no staking, and provides closely spaced internodes of the foliage leaves.

(8) A luxurious inflorescence with relatively closely spaced flowers which reasonably fill the relatively small center opening formed by a large number of small bracts having short petioles.

The accompanying illustration forming a part of this specification, graphically shows this new variety in color at full maturity or optimum, the illustration being a face view of the involucre of the subject plant from an elevated position.

The colors referred to herein correspond approximately with the colors shown in "Dictionary of Color" by Maerz and Paul (first edition, 1930), and identified by the commonly used color name, as well as the plate of said color standard in a recapitulation in tabular form herein.

The following is a more detailed description of this new variety of poinsettia plant:

*Parentage*

This new variety of poinsettia plant was originated by me as a hybrid seedling by selective hybridization of two varieties of poinsettia plants having desirable known selective properties, the seed parent being an unnamed, unpatented seedling of a variety known as Ruth Ecke (unpatented), and the pollen parent being known in the trade as Ecke White, which also is unpatented, but which in turn was a sport-parent of white variety of Ecke Patent No. 1,802, dated Jan. 20, 1959. Both the Ruth Ecke and the Ecke White poinsettia plants are well known in the trade by those names.

*Propagation*

This new variety of poinsettia plant was developed by me by the aforesaid hybridization in a cultivated area of a glass house or greenhouse at my experimental and growing gardens at Encinitas, Calif. It has been asexually reproduced and cultivated by me at my said experimental gardens, by cuttings, and successive asexual reproductions thereof by such cuttings have remained true to type and to the herein described characteristics through the propagation, cultivation and asexual reproduction thereof through several generations. Successive generations have shown its qualities and characteristics as herein set forth to be permanently fixed.

For the late fall and Christmas maturity season, such original propagation is preferably accomplished by slipping cuttings in August and early September, but although it is considered a tall grower, it is also a fast grower and it may be propagated until the end of September, and still produce a commercially sealable blooming plant by Christmas. The cuttings root reasonably fast and within about 20 days the cuttings are well rooted and can be transferred to individual pots, and in 60 to 75 days thereafter the optimum should be reached for growth of stalk, bracts, inflorescence and foliage leaves. The specifications of propagation exemplified herein are for optimum growth and production of bracts in the late fall and Christmas season, and assuming light conditions of the Northern Hemisphere and greenhouse cultivation, where temperatures are maintained around 60 to 75 degrees F. It may be here noted however, that wth greenhouse propagation which may be controlled as to light, temperature, fertilizers, environment, and chemical controls, planting of cuttings may be successfully planted at almost any time of year, allowing approximately 20 to 30 days for rooting and transplanting and 60 to 75 days thereafter (a total of approximately 80 to 100 days from planting cuttings), for optimum of bracts, inflorescence and foliage leaves.

*Structure of plant*

This new variety roots only reasonably fast, but after rooting it has an exceptionally strong, vigorous and extensive root system. It would be classed as a tall grower, at an average of 36 inches in height of peduncle at maturity from ground level to bract involucre. It has rapid growth to maturity and cuttings planted as late as the end of September will mature to an optimum for the Christmas trade. The peduncle is thin, strong and stiff, and requires no staking. It thus stands erect by itself and amply supports the weight of the bract involucre, which is a substantial advantage in an indoor plant, since stakes or an artificial crutch spoil the aesthetic effect of an indoors plant.

The structure of the bracts, inflorescence, and foliage leaves is more appropriately described under those headings, since they are the predominating visible elements of novelty in this new variety.

*Involucre of bracts*

An involucre of bracts grows at the free axial end of the peduncle. The bracts, though varying in size, are numerically plentiful and overlap extensively, providing an unbroken wreath of bracts around the inflorescence.

The individual bracts have substantially contrasting shapes and sizes, and the petioles of the bracts vary in length, the larger bracts having long petioles, the intermediate size bracts having relatively shorter petioles, and still smaller bracts approaching sub-acaulescence.

The difference in sizes of bracts and length of petioles provides an irregularity in shape and size of the opening at the center of the involucre within which the inflorescence grows, but the numerical predominance of smaller bracts with short or sub-acaulescent petioles spaces the involucre quite closely around the inflorescence.

In shape, the larger bracts which have the longest petioles, are relatively broad and oblate, and the intermediate size bracts are narrower and reasonably ovally oblate, while the still smaller sub-acaulescent bracts are essentially prolate. All bracts have a pointed tip at the outer terminal free ends thereof.

An occasional bract may have an oakleaf shield shape at its outer end, but this is not a predominant characteristic of this new variety.

In texture the bracts are flexible, which, taken with a peduncle which requires no staking, greatly enhances the shipping facility of the plant. This new variety is considered a mid-season bloomer, and the bracts, together with the inflorescence and the foliage leaves, may be brought to optimum of maturity at mid-December, but the plant is especially characterized by the extended long-keeping quality of the bracts, inflorescence and foliage leaves, which frequently last four to five weeks at optimum of floral condition.

The coloring of the bracts is quite uniform throughout all bracts of the involucre, being solid and deep in body color, but the coloring is not as bright and scintillating as the well known variety Barbara Ecke Supreme (Plant Patent No. 1,055, Dec. 18, 1951), though the fullness of the wreath of the involucre establishes a superiority of appearance as compared with the involucre of somewhat similarly colored poinsettia plants, including the Barbara Ecke Supreme. The color tone of the bracts is not dull, but may be characterized as having a subdued brilliance.

The color of the bracts is a subdued, deep rich, dark reddish-pink, tinted with rose mauve.

The venation of the bracts is of the herring-bone type which is quite distinctly prominent in the largest bracts and less prominent in the smaller bracts.

In general appearance of face view as shown in the accompanying illustration, the involucre though having numerous overlapping bracts of varying sizes, is unusually symmetrical in a fairly uniform periphery, somewhat resembling the physical form of the involucre of numerous overlapping bracts of varying sizes of Ecke Plant Patent No. 1,779, dated Dec. 9, 1958.

*Inflorescence*

In the center of the bract involucre is an open space formed by the length of petioles of the bracts. In this new variety this center opening is not excessively large, due to the relatively short petioles of a large number of smaller bracts. In the center opening there sprout pale green spurs at the free terminal axial end of the peduncle. Upon these spurs are formed the sub-acaulescent inflorescence which is plentiful and closely clustered to substantially fill such central opening of the bract involucre. The individual flowers in the inflorescence are of the usual type, having pale green cyathia, with flower cups of orange-yellow. The center portion of the flower is a dark rose pink substantially similar to the color of the bracts.

*Foliage leaves*

The foliage leaves of this new variety are arranged around the peduncle, the nodes thereof being quite uniformly spaced. Though the plant may be classed as a tall grower, the foliage leaves are numerous and reasonably close together, averaging approximately four inches apart in the nature of a helix. Their spacing however, is somewhat dependent on the rapidity of growth of the plant. Like the bracts, the foliage leaves hold tenaciously to the peduncle, and in shape they are quite uniformly of the ovate, i.e., oval acuminate type.

Those foliage leaves which are spaced remotely from the bracts are dark ivy green in color, whereas those closely adjacent to the bracts are likely to be of a substantialy similar dark ivy green color with a tint of pink in spots.

The venation of the foliage leaves is of herring-bone type, perceptible but not accentuated.

*Immunity*

Having a large vigorous root, this new variety is hardy and healthy in growth. It appears to have an unusual resistance to some of the diseases which frequently are present in poinsettia plants, cultivated in the area of Encinitas, Calif., where the present new variety was developed. More particularly, this new variety is unusually resistant to a stem rot disease condition which is usually recognized as being caused by a root fungus designated rhizoctonia, and is also unusually resistant to a root rot condition caused by a fungus thielaviopsis, the detrimental factors of which are principally evidenced by leaf-drop of the foliage prior to complete maturity of the bract involucre and inflorescence. This resistance to disease and detrimental factors has been observed in this new variety when it has been grown side-by-side with other existing known varieties under the same soil, temperature and moisture conditions at Encinitas, Calif.

*Variations*

Individual plants of this new variety have an unusual similarity, and successive asexually reproduced generations exhibit adherence to characteristics and type herein described. However, there may be some variation in the characteristics of minor details, in the comparison of plant grown in different localities, in different soils, at different times of the year, varying temperatures, varying types of glass house, or out-of-doors, or because of treatment with light or chemicals. The conditions set forth herein are especially pertinent and prevalent in conditions of propagation and cultivation at my experimental gardens at Encinitas, which is in southern California, where, in field conditions, the nighttime temperature frequently goes down into the lower forties F., whereas with plants growing in a greenhouse, the temperature is preferably maintained practically uniform around 60 to 75 degrees F.

*Color tabulation*

The color designations according to the color plates of the aforesaid "Dictionary of Color" are recapitulated in tabular form as follows:

| Part of Plant | Non-Technical Designation of Color | Dictionary of Color | | |
|---|---|---|---|---|
| | | Plate | Letter | Number |
| Peduncle | Greenish-brown | 8 | L | 6 |
| Bracts | Subdued reddish-pink, rose tinted with mauve. | 52 | L | 4 |
| Foliage leaves: | | | | |
| (a) Remote from bracts. | Ivy green | 32 | H | 1 |
| (b) Adjacent to bracts. | Mainly ivy green, slightly spotted pink. | 32 | C | 1 |
| Inflorescence: | | | | |
| (a) Cyathium | Pale green | 20 | G | 1 |
| (b) Flower | Orange yellow | 10 | L | 7 |
| (c) Center portion | Dark rose pink | 51 | L | 8 |
| (d) Spurs mounting inflorescence. | Pale green | 20 | G | 1 |

Having described the invention, I claim:

A new and distinct variety of poinsettia plant, as illustrated and described, and more particularly characterized by an involucre of flexible bracts which have a color of subdued reddish-pink, rose-tinted with mauve, the bracts being numerically plentiful and varying in shape and planar size, the bracts of largest size being oblate, bracts of intermediate size being generally ovally oblate, and bracts of still smaller size being generally prolate, the length of the petioles of the bracts being of respective lengths in the same order of the said sizes of the bracts, the bracts of intermediate and smaller sizes being predominant in number and the relatively shorter petioles thereof providing an opening centrally of the involucre wherein there grows a luxuriant and closely clustered inflorescence, the plant being a relatively fast-growing tall variety which is naturally an early bloomer, and having exceptionally long-keeping bracts, inflorescence and foliage leaves at optimum condition, the peduncle being stiff and strong and having internodes closely spaced for ovally acuminate ivy green foliage leaves.

No references cited.

ABRAHAM G. STONE, *Primary Examiner.*

ROBERT E. BAGWILL, *Examiner.*